(12) United States Patent
Kim et al.

(10) Patent No.: US 12,157,764 B2
(45) Date of Patent: Dec. 3, 2024

(54) DOSING REGIMEN FOR TREATING INFLUENZA VIRUS DISEASES

(71) Applicant: CELLTRION INC., Incheon (KR)

(72) Inventors: Sung Hyun Kim, Incheon (KR); Hyun Chul An, Incheon (KR); Sang Joon Lee, Incheon (KR); Se Won Lee, Incheon (KR); Da Bee Jeon, Incheon (KR)

(73) Assignee: CELLTRION INC., Incheon (KR)

( * ) Notice: Subject to any disclaimer, the term of this patent is extended or adjusted under 35 U.S.C. 154(b) by 727 days.

(21) Appl. No.: 17/294,907

(22) PCT Filed: Nov. 22, 2019

(86) PCT No.: PCT/KR2019/016194
§ 371 (c)(1),
(2) Date: May 18, 2021

(87) PCT Pub. No.: WO2020/106116
PCT Pub. Date: May 28, 2020

(65) Prior Publication Data
US 2021/0403539 A1 Dec. 30, 2021

(30) Foreign Application Priority Data
Nov. 23, 2018 (KR) .................. 10-2018-0146218

(51) Int. Cl.
*C07K 16/10* (2006.01)
*A61K 39/00* (2006.01)

(52) U.S. Cl.
CPC .... *C07K 16/1018* (2013.01); *A61K 2039/505* (2013.01); *A61K 2039/545* (2013.01)

(58) Field of Classification Search
CPC .......... C07K 16/1018; A61K 2039/505; A61K 2039/545
See application file for complete search history.

(56) References Cited

U.S. PATENT DOCUMENTS

| | | | |
|---|---|---|---|
| 4,861,335 A | 8/1989 | Reynolds | |
| 5,085,642 A | 2/1992 | Sarnoff et al. | |
| 5,681,291 A | 10/1997 | Galli | |
| 6,331,174 B1 | 12/2001 | Reinhard et al. | |
| 9,573,991 B2 * | 2/2017 | Chang ................ | A61P 31/16 |
| 2014/0234336 A1 * | 8/2014 | Chang .............. | G01N 33/56983 |
| | | | 435/339 |
| 2016/0052997 A1 * | 2/2016 | Hong ................. | A61K 31/215 |
| | | | 424/139.1 |
| 2016/0176953 A1 | 6/2016 | Purcell Ngambo et al. | |
| 2021/0347861 A1 | 11/2021 | Lee et al. | |

FOREIGN PATENT DOCUMENTS

| | | | |
|---|---|---|---|
| CN | 105338994 A | 2/2016 | |
| CN | 108064240 A | 5/2018 | |
| EP | 3011968 A1 | 4/2016 | |
| KR | 1020050111336 A | 11/2005 | |
| KR | 1020080106433 A | 12/2008 | |
| KR | 10-20110102198 A | 9/2011 | |
| KR | 10-20130035916 A | 4/2013 | |
| KR | 10-20140119641 A | 10/2014 | |
| KR | 1020140118682 A | 10/2014 | |
| KR | 10-1605573 B1 | 3/2016 | |
| KR | 1020160132020 A | 11/2016 | |
| KR | 10-20180018393 A | 2/2018 | |
| WO | WO-2015120097 A2 * | 8/2015 | ............. A61K 39/42 |
| WO | 2018030777 A1 | 2/2018 | |

OTHER PUBLICATIONS

Wu et al. A potent broad-spectrum protective human monoclonal antibody crosslinking two haemagglutinin monomers of influenza A virus. Nat Commun. Jul. 21, 2015;6:7708. (Year: 2015).*
Yang, et al., "Phase IIb study evaluating the efficacy and safety of anti-influenza A monoclonal antibody, CT-P27, in subjects with acute uncomplicated Influenza A Infection," 29th EDDMID, Amsterdam, Netherlands, Apr. 16, 2019.
Sparrow, et al., "Passive immunization for influenza through antibody therapies, a review of the pipeline, challenges and potential applications," Vaccine, vol. 34, No. 45, Sep. 9, 2016, pp. 5442-5448.
Supplementary European Search Report and European Search Opinion for EP 19887601.3, dated Jan. 19, 2022.

* cited by examiner

*Primary Examiner* — Janet L Andres
*Assistant Examiner* — Ruixue Wang
(74) *Attorney, Agent, or Firm* — BakerHostetler

(57) ABSTRACT

The present invention pertains to a dosing regimen for treating influenza virus diseases, and more specifically, to a method for treating influenza virus-related diseases through the administration of a mixed composition of monoclonal antibodies having a neutralizing activity against the influenza A virus. The treatment method according to the present invention enables influenza A virus-related diseases to be treated through the intravenous administration of a mixed composition of monoclonal antibodies having a neutralizing activity against the influenza A virus. In addition, the treatment method according to the present invention can satisfy unmet medical needs for biological therapeutic agents for influenza virus-related diseases.

10 Claims, No Drawings
Specification includes a Sequence Listing.

SEQUENCE LISTING

```
<160> NUMBER OF SEQ ID NOS: 16

<210> SEQ ID NO 1
<211> LENGTH: 11
<212> TYPE: PRT
<213> ORGANISM: Artificial Sequence
<220> FEATURE:
<223> OTHER INFORMATION: CT120 light chain CDR1

<400> SEQUENCE: 1

Arg Ala Ser Glu Asn Ile Trp Asn Asn Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CT120 light chain CDR2

<400> SEQUENCE: 2

Gly Ala Ser Thr Gly Ala Thr
1               5

<210> SEQ ID NO 3
<211> LENGTH: 9
<212> TYPE: PRT
<213> ORGANISM: Artificial Sequence
<220> FEATURE:
<223> OTHER INFORMATION: CT120 light chain CDR3

<400> SEQUENCE: 3

Gln Gln Tyr Asn Ser Trp Pro Arg Thr
1               5

<210> SEQ ID NO 4
<211> LENGTH: 5
<212> TYPE: PRT
<213> ORGANISM: Artificial Sequence
<220> FEATURE:
```

```
<223> OTHER INFORMATION: CT120 heavy chain CDR1

<400> SEQUENCE: 4

Ser His Ala Ile Ser
1               5

<210> SEQ ID NO 5
<211> LENGTH: 17
<212> TYPE: PRT
<213> ORGANISM: Artificial Sequence
<220> FEATURE:
<223> OTHER INFORMATION: CT120 heavy chain CDR2

<400> SEQUENCE: 5

Gly Ile Ser Pro Met Phe Gly Thr Thr His Tyr Ala Gln Lys Phe Gln
1               5                   10                  15

Gly

<210> SEQ ID NO 6
<211> LENGTH: 14
<212> TYPE: PRT
<213> ORGANISM: Artificial Sequence
<220> FEATURE:
<223> OTHER INFORMATION: CT120 heavy chain CDR3

<400> SEQUENCE: 6

Asp Gly Ala Gly Ser Tyr Tyr Pro Leu Asn Trp Phe Asp Pro
1               5                   10

<210> SEQ ID NO 7
<211> LENGTH: 12
<212> TYPE: PRT
<213> ORGANISM: Artificial Sequence
<220> FEATURE:
<223> OTHER INFORMATION: CT149 light chain CDR1

<400> SEQUENCE: 7

Arg Ala Ser His Arg Val Gly Ser Thr Tyr Ile Ala
1               5                   10

<210> SEQ ID NO 8
<211> LENGTH: 7
<212> TYPE: PRT
<213> ORGANISM: Artificial Sequence
<220> FEATURE:
<223> OTHER INFORMATION: CT149 light chain CDR2

<400> SEQUENCE: 8

Gly Ala Ser Asn Arg Ala Thr
1               5

<210> SEQ ID NO 9
<211> LENGTH: 9
<212> TYPE: PRT
<213> ORGANISM: Artificial Sequence
<220> FEATURE:
<223> OTHER INFORMATION: CT149 light chain CDR3

<400> SEQUENCE: 9

Gln Gln Phe Ser Val Ser Pro Trp Thr
1               5

<210> SEQ ID NO 10
<211> LENGTH: 5
<212> TYPE: PRT
<213> ORGANISM: Artificial Sequence
```

-continued

```
<220> FEATURE:
<223> OTHER INFORMATION: CT149 heavy chain CDR1

<400> SEQUENCE: 10

Thr Tyr Gly Val Ser
1               5

<210> SEQ ID NO 11
<211> LENGTH: 17
<212> TYPE: PRT
<213> ORGANISM: Artificial Sequence
<220> FEATURE:
<223> OTHER INFORMATION: CT149 heavy chain CDR2

<400> SEQUENCE: 11

Trp Ile Ser Ala Tyr Thr Gly Ile Thr Asp Tyr Ala Gln Lys Phe Gln
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: CT149 heavy chain CDR3

<400> SEQUENCE: 12

Asp Lys Val Gln Gly Arg Val Glu Val Gly Ser Gly Gly Arg His Asp
1               5                   10                  15

Tyr

<210> SEQ ID NO 13
<211> LENGTH: 234
<212> TYPE: PRT
<213> ORGANISM: Artificial Sequence
<220> FEATURE:
<223> OTHER INFORMATION: CT120 light chain

<400> SEQUENCE: 13

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Glu Asn
            35                  40                  45

Ile Trp Asn Asn Leu Ala Trp Tyr Gln Gln Lys Pro Gly Gln Ala Pro
        50                  55                  60

Arg Leu Leu Ile Ser Gly Ala Ser Thr Gly Ala Thr Gly Val Pro Ser
65                  70                  75                  80

Arg Phe Arg Gly Ser Gly Ser Arg Thr Glu Phe Thr Leu Thr Ile Ser
                85                  90                  95

Ser Leu Gln Ser Glu Asp Phe Ala Ile Tyr Phe Cys Gln Gln Tyr Asn
                100                 105                 110

Ser Trp Pro Arg Thr Phe Gly Pro Gly Thr Lys Val Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
```

-continued

```
                165                 170                 175
Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 14
<211> LENGTH: 472
<212> TYPE: PRT
<213> ORGANISM: Artificial Sequence
<220> FEATURE:
<223> OTHER INFORMATION: CT120 heavy chain

<400> SEQUENCE: 14

Met Asp Trp Thr Trp Arg Phe Leu Phe Val Val Ala Ala Ala Thr Gly
1               5                   10                  15

Val Gln Cys Gln Val Gln Leu Val Gln Ser Gly Ala Glu Val Lys Met
            20                  25                  30

Pro Gly Ser Ser Val Lys Val Ser Cys Lys Thr Ser Gly Val Phe Phe
        35                  40                  45

Ser Ser His Ala Ile Ser Trp Val Arg Gln Ala Pro Gly Gln Gly Leu
    50                  55                  60

Glu Trp Met Gly Gly Ile Ser Pro Met Phe Gly Thr Thr His Tyr Ala
65                  70                  75                  80

Gln Lys Phe Gln Gly Arg Val Thr Ile Thr Ala Asp Gln Ser Thr Thr
                85                  90                  95

Thr Ala Tyr Met Glu Leu Thr Ser Leu Thr Ser Glu Asp Thr Ala Val
            100                 105                 110

Tyr Tyr Cys Ala Arg Asp Gly Ala Gly Ser Tyr Tyr Pro Leu Asn Trp
        115                 120                 125

Phe Asp Pro Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Arg Glu Val Thr Cys Val Val
        275                 280                 285

Val Asp Val Ser His Glu Asp Pro Glu Val Lys Phe Asn Trp Tyr Val
```

```
            290                 295                 300
Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Gly Leu His Asn His Tyr Thr Gln Lys
    450                 455                 460

Ser Leu Ser Leu Phe Pro Gly Lys
465                 470

<210> SEQ ID NO 15
<211> LENGTH: 215
<212> TYPE: PRT
<213> ORGANISM: Artificial Sequence
<220> FEATURE:
<223> OTHER INFORMATION: CT149 light chain

<400> SEQUENCE: 15

Glu Val Val Leu Thr Gln Ser Pro Gly Thr Leu Ala Leu Pro Pro Gly
1               5                   10                  15

Glu Arg Ala Thr Leu Ser Cys Arg Ala Ser His Arg Val Gly Ser Thr
            20                  25                  30

Tyr Ile Ala Trp Tyr Gln Gln Lys Ser Gly Gln Ala Pro Arg Arg Leu
        35                  40                  45

Ile Tyr Gly Ala Ser Asn Arg Ala Thr Asp Ile Pro Asp Arg Phe Ser
    50                  55                  60

Gly Ser Gly Ser Gly Thr Asp Phe Thr Leu Thr Ile Arg Arg Leu Glu
65                  70                  75                  80

Pro Glu Asp Ser Ala Val Tyr Tyr Cys Gln Gln Phe Ser Val Ser Pro
                85                  90                  95

Trp Thr Phe Gly Gln Gly Thr Arg Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
```

```
                        180                 185                 190
Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 16
<211> LENGTH: 456
<212> TYPE: PRT
<213> ORGANISM: Artificial Sequence
<220> FEATURE:
<223> OTHER INFORMATION: CT149 heavy chain

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Ser Phe Ser Thr Tyr
            20                  25                  30

Gly Val Ser Trp Val Arg Gln Ala Pro Gly Gln Gly Pro Glu Trp Val
        35                  40                  45

Gly Trp Ile Ser Ala Tyr Thr Gly Ile Thr Asp Tyr Ala Gln Lys Phe
    50                  55                  60

Gln Gly Arg Val Thr Leu Thr Thr Asp Ala Thr Thr Ala Thr Ala Phe
65                  70                  75                  80

Leu Asp Leu Arg Ser Leu Arg Pro Asp Asp Thr Ala Thr Tyr Phe Cys
                85                  90                  95

Ala Arg Asp Lys Val Gln Gly Arg Val Glu Val Gly Ser Gly Gly Arg
            100                 105                 110

His Asp Tyr Trp Gly Gln Gly Thr Leu Val Ile Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
```

-continued

```
                325                 330                 335
Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
        420                 425                 430

Ser Cys Ser Val Met His Glu Gly Leu His Asn His Tyr Thr Gln Lys
        435                 440                 445

Ser Leu Ser Leu Ser Pro Gly Lys
    450                 455
```

DOSING REGIMEN FOR TREATING INFLUENZA VIRUS DISEASES

CROSS-REFERENCE TO RELATED APPLICATIONS

This application is a National Stage of International Patent Application No. PCT/KR2019/016194, filed on Nov. 22, 2019, which claims priority to Korean Patent Application No. KR 10-2018-0146218, filed on Nov. 23, 2018, the disclosures of which are incorporated by reference in their entireties.

SEQUENCE LISTING

The instant application contains a Sequence Listing which has been filed electronically in ASCII format and is hereby incorporated by reference in its entirety. Said ASCII copy, created on May 18, 2021, is named FC21107US_SL_ST25.txt and is 14,973 bytes in size.

TECHNICAL FIELD

The present disclosure relates to a method for treating influenza virus-related diseases through the administration of a mixed composition of monoclonal antibodies having a neutralizing activity against the influenza A virus.

BACKGROUND ART

Influenza is a respiratory disease caused by influenza virus infection, causing an epidemic in winter every year, and it is known that the elderly and children are particularly vulnerable. Influenza viruses are classified into types A, B, and C, of which types A and B are transmitted to humans or animals. Influenza A virus may be further subdivided into various subtypes according to antigens HA (Hemagglutinin) and NA (Neuraminidase) present on a virus surface (H1N1, H3N2, etc.), and there is no influenza B virus subdivided according to subtype. Viruses with various subtypes may be generated through a combination of 17 types of HA and 10 types of NA of influenza A virus known to date.

However, it is estimated that the conventional formulations as described above may be related to the development of resistant virus strains. In addition, no biological therapeutic agent has been approved to date for subjects with influenza A infection having no combinations or influenza A infection accompanied by serious and life-threatening complications.

Accordingly, the present applicant has completed a liquid pharmaceutical formulation for intravenous administration, comprising a mixture of two or more different anti-influenza virus antibodies or antigen-binding fragments thereof, which are believed to neutralize viral activity by binding to the conserved stem portion of the influenza A virus HA.

However, a safe and effective optimal dosing regimen for treating influenza virus diseases continues to be needed.

DISCLOSURE

Technical Problem

An object of the present disclosure is to provide a therapeutic method wherein a composition comprising a mixture of two or more different anti-influenza virus antibodies or antigen-binding fragments thereof is administered to a patient for the treatment of influenza virus-related diseases.

In addition, another object of the present disclosure is to provide a pharmaceutical composition for treating influenza virus-related diseases, comprising a mixture of two or more different anti-influenza virus antibodies or antigen-binding fragments thereof.

In addition, another object of the present disclosure is to provide a kit comprising (a) a composition comprising a mixture of two or more different anti-influenza virus antibodies or antigen-binding fragments thereof; and (b) instructions directed for administering a mixture of the antibody or antigen-binding fragment thereof to treat a patient with influenza virus-related diseases.

In addition, another object of the present disclosure is to provide a use of a mixture of anti-influenza virus antibodies or antigen-binding fragments thereof, in the preparation of a pharmaceutical composition for treating influenza virus-related diseases by administering the pharmaceutical composition to a patient.

Technical Solution

The present disclosure provides a method for treating influenza virus-related diseases, comprising administering to a patient a composition comprising a mixture of two or more different anti-influenza virus antibodies or antigen-binding fragments thereof, wherein the mixture of antibodies or antigen binding fragments thereof is administered to the patient at a dose of 10 to 120 mg/kg.

In one embodiment of the present disclosure, the mixture of antibodies or antigen-binding fragments thereof is administered to the patient at a dose of 10, 20, 30, 40, 50, 60, 70, 80, 90, 100, 110, 120 mg/kg.

In one embodiment of the present disclosure, the mixture of antibodies or antigen-binding fragments thereof may be administered to the patient at a dose of 30 to 110 mg/kg.

In one embodiment of the present disclosure, the mixture of antibodies or antigen-binding fragments thereof may be administered to the patient at a dose of 40 to 100 mg/kg.

In one embodiment of the present disclosure, the mixture of antibodies or antigen-binding fragments thereof may be administered to the patient at a dose of 45 to 90 mg/kg.

In one embodiment of the present disclosure, the mixture of antibodies or antigen-binding fragments thereof may be administered intravenously.

In one embodiment of the present disclosure, the mixture of antibodies or antigen-binding fragments thereof may be intravenously administered to a patient for ninety (90) minutes.

In one embodiment of the present disclosure, the mixture of two or more different anti-influenza virus antibodies or antigen-binding fragments thereof may comprise antibodies or antigen-binding fragments thereof comprising a light chain variable region comprising a CDR1 region of SEQ ID NO: 1, a CDR2 region of SEQ ID NO: 2, and a CDR3 region of SEQ ID NO: 3, and a heavy chain variable region comprising a CDR1 region of SEQ ID NO: 4, a CDR2 region of SEQ ID NO: 5, and a CDR3 region of SEQ ID NO: 6; and antibodies or antigen-binding fragments thereof comprising a light chain variable region comprising a CDR1 region of SEQ ID NO: 7, a CDR2 region of SEQ ID NO: 8, and a CDR3 region of SEQ ID NO: 9, and a heavy chain variable region comprising a CDR1 region of SEQ ID NO: 10, a CDR2 region of SEQ ID NO: 11, and a CDR3 region of SEQ ID NO: 12.

In one embodiment of the present disclosure, the mixture of two or more different anti-influenza virus antibodies or antigen-binding fragments thereof may comprise antibodies or an antigen-binding fragments thereof comprising a light chain variable region of the polypeptide sequence of SEQ ID NO 13 and a heavy chain variable region of the polypeptide sequence of SEQ ID NO 14; and antibodies or antigen-binding fragments thereof comprising the light chain variable region of the polypeptide sequence of SEQ ID NO: 15 and the heavy chain variable region of the polypeptide sequence of SEQ ID NO: 16.

In one embodiment of the present disclosure, the mixture of antibodies or antigen-binding fragments thereof may be administered in combination with zanamivir, oseltamivir, laninamivir, peramivir, rimantadine, amantadine, ribavirin, or a mixture thereof.

In one embodiment of the present disclosure, influenza virus-related diseases may cause at least one symptom selected from the group consisting of cough, headache, fever, muscle pain, rhinorrhea, nasal congestion, chills, fatigue, weakness, shortness of breath, vomiting, pain, diarrhea, pneumonia, and bronchitis caused by the influenza virus.

In one embodiment of the present disclosure, a composition comprising a mixture of two or more different anti-influenza virus antibodies or antigen-binding fragments thereof may comprise (A) a mixture of two or more different anti-influenza virus antibodies or antigen-binding fragments thereof; (B) a surfactant; (C) sugar or a sugar derivative; and (D) an amino acid.

In one embodiment of the present disclosure, when (A) the mixture of two or more different anti-influenza virus antibodies is a mixture of two different antibodies, a mixing ratio of the two different antibodies may be 9:1 to 1:9.

In one embodiment of the present disclosure, the concentration of (A) the mixture of two or more different anti-influenza virus antibodies may be 10 to 120 mg/mL.

In one embodiment of the present disclosure, (B) the surfactant may include polysorbate, poloxamer, or a mixture thereof.

In one embodiment of the present disclosure, (B) the surfactant may include polysorbate 20, polysorbate 40, polysorbate 60, polysorbate 80, or a mixture of two or more thereof.

In one embodiment of the present disclosure, (B) the surfactant may include polysorbate 80.

In one embodiment of the present disclosure, the concentration of (B) the surfactant may be 0.01 to 1.0% (w/v).

In one embodiment of the present disclosure, (C) sugar may include a monosaccharide, a disaccharide, an oligosaccharide, a polysaccharide, or a mixture of two or more thereof.

In one embodiment of the present disclosure, (C) a sugar derivative may include a sugar alcohol, a sugar acid, or a mixture thereof.

In one embodiment of the present disclosure, (C) a sugar may include a monosaccharide, disaccharide, oligosaccharide, polysaccharide or a mixture of two or more thereof and (C) a sugar derivative may include a sugar alcohol, a sugar acid, or a mixture thereof.

In one embodiment of the present disclosure, (C) the sugar or the sugar derivative may include sorbitol, mannitol, trehalose, sucrose or a mixture of two or more thereof.

In one embodiment of the present disclosure, the concentration of (C) the sugar or the sugar derivative may be 0.1 to 15% (w/v).

In one embodiment of the present disclosure, (D) the amino acid may include a free amino acid, a salt of the amino acid or a mixture thereof.

In one embodiment of the present disclosure, (D) the amino acid may include aspartic acid, histidine, lysine, arginine or a salt thereof.

In one embodiment of the present disclosure, (D) the amino acid may include histidine, a salt of the histidine or a mixture thereof.

In one embodiment of the present disclosure, the concentration of (D) the amino acid may be 1 to 20 mM.

In one embodiment of the present disclosure, the pH may be 5.5 to 6.5.

In one embodiment of the present disclosure, the purity of the antibody monomer measured after storage at 40±2° C. for 6 weeks may be 95% or more.

In one embodiment of the present disclosure, the purity of the antibody monomer measured after storage for three (3) months or more at a condition of 5±3° C./ambient relative humidity may be 95% or more.

In one embodiment of the present disclosure, the purity of the antibody monomer measured after storage for six (6) months or more at a condition of 5±3° C./ambient relative humidity may be 95% or more.

In one embodiment of the present disclosure, the composition may be for intravenous, intramuscular, intradermal, subcutaneous, intraperitoneal, topical administration, or a combination thereof.

In one embodiment of the present disclosure, a composition comprising a mixture of two or more different anti-influenza virus antibodies or antigen-binding fragments thereof may comprise (A) 10 to 120 mg/mL of a mixture of two or more different anti-influenza virus antibodies or antigen-binding fragments thereof, (B) 0.01 to 1.0% (w/v) of polysorbate 80; (C) 0.1 to 15% (w/v) of sorbitol, and (D) 1 to 20 mM of histidine.

In one embodiment of the present disclosure, the patient after administering a mixture of the antibody or antigen-binding fragment thereof, may have one or more of the following characteristics.
   a) Symptoms such as cough, sore throat or stuffy nose which are respiratory symptoms are mild or absent for at least 24 hours.
   b) Symptoms such as headache, fever, pain, or fatigue which are systemic symptoms are mild or absent for at least 24 hours.
   c) The body temperature is maintained not more than 37.8° C. for at least 24 hours.

In one embodiment of the present disclosure, patients before administering a mixture of antibodies or antigen-binding fragments thereof may have one or more of the following characteristics.
   a) patients with two or more of respiratory symptoms such as cough, sore throat, or stuffy nose, or systemic symptoms such as headache, fever, induced pain, and fatigue.
   b) patients with high fever of 38.0° C. (100.4° F.) or more at screening, or high fever within 24 hours before screening, but receiving antipyretic treatment within 6 hours before screening.
   c) patients who do not have a history of administration of an antiviral agent within 14 days prior to administration of the mixture.

In addition, the present disclosure provides a pharmaceutical composition for treating influenza virus-related diseases, comprising a mixture of two or more different anti-influenza virus antibodies or antigen-binding fragments thereof.

Further, the present disclosure provides a kit comprising:
(a) a composition comprising a mixture of two or more different anti-influenza virus antibodies or antigen-binding fragments thereof; and (b) instructions directed for administering a mixture of the antibody or antigen-binding fragment thereof to treat a patient with an influenza virus-related disease.

Furthermore, the present disclosure provides a use of a mixture of anti-influenza virus antibodies or antigen-binding fragments thereof in the preparation of a pharmaceutical composition for treating influenza virus-related diseases by administering the pharmaceutical composition to a patient.

Advantageous Effects

A treatment method, composition, kit or use according to the present disclosure enables influenza A virus-related diseases to be treated through the intravenous administration of a mixed composition of monoclonal antibodies having a neutralizing activity against the influenza A virus. In addition, the treatment method according to the present disclosure can satisfy unmet medical needs for biological therapeutic agents for influenza virus-related diseases.

MODE FOR INVENTION

The present disclosure relates to a method for treating influenza virus-related diseases through the intravenous administration of a mixed composition of monoclonal antibodies having a neutralizing activity against the influenza A virus. A variety of aspects of the present disclosure relates to a treatment with antibodies and antigen-binding fragments thereof and a pharmaceutical composition comprising the same.

In order to more easily understand the present disclosure, the terms used in the present disclosure will be defined below.

In the present disclosure, an "antibody" is used in its broadest sense and may comprise polyclonal antibodies, monoclonal antibodies, recombinant antibodies, single chain antibodies, hybrid antibodies, chimeric antibodies, humanized antibodies, human antibodies, or fragments thereof. Other naturally occurring antibodies with altered structures, such as camelid antibodies, are also included in this definition. An intact antibody refers to an immunoglobulin molecule consisting of four polypeptide chains wherein two heavy chains and two light chains are linked to each other by a disulfide bond. Fragments of antibodies comprise in particular Fab, F(ab'), F(ab')2, Fv, dAb, Fd, complementarity determining region (CDR) fragment, single-chain antibody (scFv), bivalent single-chain antibody, single-chain phage antibody, diabody, triabody, tetrabody, polypeptide containing one or more fragments of immunoglobulin sufficient to bind a specific antigen to the polypeptide, etc. Each heavy chain consists of a heavy chain variable region and a heavy chain constant region. The heavy chain constant region consists of three domains (CH1, CH2, and CH3). Each light chain consists of a light chain variable region and a light chain constant region. The light chain constant region consists of one domain (CL). The heavy chain variable region and the light chain variable region may be further subdivided into a hypervariable region called a complementarity determining region (CDR), which is arranged together with a more conserved region called a framework region (FR). Each of the heavy and light chain variable regions consists of three CDRs and four FRs, which are arranged in the following order from the amino terminus to the carboxy terminus: FR1, CDR1, FR2, CDR2, FR3, CDR3, FR4.

In the present disclosure, the CDR of the variable region was determined by a conventional method according to a system devised by Kabat et al. (see, Kabat et al., Sequences of Proteins of Immunological Interest (5th), National Institutes of Health, Bethesda, MD. (1991)). The CDR numbering used in the present disclosure used a Kabat method, but antibodies containing CDRs determined according to other methods such as an IMGT method, a Chothia method, and an AbM method are also included in the present disclosure.

In the present disclosure, the antibody includes functional variants of the antibody. If functional variants of the antibody may compete with the antibody of the present disclosure for specifically binding to the influenza virus, it is considered a functional variant of the antibody of the present disclosure. Functional variants may comprise derivatives having substantially similar primary structural sequences, but are not limited thereto. The functional variant may be an antibody comprising an amino acid sequence comprising substitutions, insertions, deletions, or combinations thereof of one or more amino acids, optionally compared to the amino acid sequence of the parent antibody. Furthermore, functional variants may comprise a truncated form of the amino acid sequence at either or both the amino terminus or the carboxy terminus. Functional variants of the present disclosure may have the same or different, higher or lower binding affinity compared to the parental antibodies of the present disclosure, but are still capable of binding to influenza virus. Functional variants within the scope of the present disclosure can have about 50 to 99%, about 60 to 99%, about 80 to 99%, about 90 to 99%, about 95 to 99%, or about 97 to 99% amino acid sequence identity with the disclosed antibodies. In order to optimally align the amino acid sequences to be compared and to define similar or identical amino acid residues, Gap or Bestfit, etc., known to those skilled in the art among computer algorithms may be used. Functional variants may be obtained by changing the parent antibody or a part thereof with known general molecular biology methods including a PCR method, mutagenesis using oligomeric nucleotides and partial mutagenesis, or by organic synthesis methods, but are not limited thereto.

In the present disclosure, an "antigen-binding fragment" refers to one or more fragments of an antibody that retain the ability to specifically bind to an antigen bound by an intact antibody. Exemplary antigen binding fragments include, but are not limited to, Fab, Fab', F(ab')2, Fv, etc.

In the present disclosure, a "mixture" refers to a substance in which two or more types of substances do not cause a chemical reaction and are simply mixed physically.

In the present disclosure, "administration" refers to administration of a substance (e.g., an anti-influenza virus antibody mixture) to achieve a therapeutic purpose (e.g., influenza virus-related diseases).

In the present disclosure, an "influenza A virus" is an enveloped virus belonging to Orthomyxoviridae, which has a genome of RNA (ribonucleic acid) of negative-polarity, single-strands composed of eight segments, is classified into groups A, B, and C, and is again divided into several subtypes according to major surface proteins, HA (hemagglutinin) and NA (neuraminidase). To date, 17 types of HA and 10 types of NA have been known.

In the present disclosure, a "subject" includes all human or non-human animals. The term "non-human animals" includes, but is not limited to, vertebrates such as non-human primates, sheep, dogs, cats, rabbits and ferrets, rodents such as mice, rats and guinea pigs, bird species such as chickens, amphibians, and reptiles. In a preferred embodiment, the subject is a mammal, such as a non-human primate, sheep, dog, cat, rabbit, ferret, or rodent. In a more preferred embodiment, the subject is a human. The terms "subject", "patient" and "individual" are used interchangeably herein.

In the present disclosure, a "kit" refers to a packaged product containing components for administering a mixture of anti-influenza A virus antibodies or antigen-binding fragments thereof of the present disclosure for the treatment of influenza A virus-related diseases. The kit preferably includes a container or box holding the components of the kit. The box or container is accompanied by a protocol or label approved by the Food and Drug Administration. The box or container holds the components of the present disclosure contained within a plastic, polyethylene, polypropylene, ethylene, or propylene container. The container may be a tube or bottle with a lid. The kit also includes instructions for administering a mixture of anti-influenza virus antibodies or antigen binding fragments thereof of the present disclosure.

Various aspects of the present disclosure will be described in further detail herein.

Two or More Different Anti-Influenza Virus Antibodies or Antigen-Binding Fragments Thereof of Present Disclosure In one embodiment of the present disclosure, the mixture of two or more different anti-influenza virus antibodies or antigen-binding fragments thereof is polyclonal antibodies, monoclonal antibodies, recombinant antibodies, single chain antibodies, hybrid antibodies, chimeric antibodies, humanized antibodies or fragments thereof, as an antibody.

In another embodiment of the present disclosure, a mixture of two or more different anti-influenza virus antibodies or antigen-binding fragments thereof may comprise human antibodies.

In another embodiment of the present disclosure, a mixture of two or more different anti-influenza virus antibodies or antigen-binding fragments thereof may be included in a class of IgG of the antibody.

In another embodiment of the present disclosure, a mixture of two or more different anti-influenza virus antibodies or antigen-binding fragments thereof may comprise antibodies or antigen-binding fragments thereof comprising a light chain variable region comprising a CDR1 region of SEQ ID NO: 1, a CDR2 region of SEQ ID NO: 2, and a CDR3 region of SEQ ID NO: 3, and a heavy chain variable region comprising a CDR1 region of SEQ ID NO: 4, a CDR2 region of SEQ ID NO: 5, and a CDR3 region of SEQ ID NO: 6; and antibodies or antigen-binding fragments thereof comprising a light chain variable region comprising a CDR1 region of SEQ ID NO: 7, a CDR2 region of SEQ ID NO: 8, and a CDR3 region of SEQ ID NO: 9, and a heavy chain variable region comprising a CDR1 region of SEQ ID NO: 10, a CDR2 region of SEQ ID NO: 11, and a CDR3 region of SEQ ID NO: 12.

In another embodiment of the present disclosure, a mixture of two or more different anti-influenza virus antibodies or antigen-binding fragments thereof may comprise antibodies or antigen-binding fragments thereof comprising a light chain variable region of the polypeptide sequence of SEQ ID NO 13 and a heavy chain variable region of the polypeptide sequence of SEQ ID NO 14; and antibodies or antigen-binding fragments thereof comprising the light chain variable region of the polypeptide sequence of SEQ ID NO: 15 and the heavy chain variable region of the polypeptide sequence of SEQ ID NO: 16.

Composition Comprising Mixture of Two or More Different Anti-Influenza Virus Antibodies or Antigen-Binding Fragments Thereof of Present Disclosure As used herein, the term "composition comprising a mixture of two or more different anti-influenza virus antibodies or antigen-binding fragments thereof of the present disclosure" is used interchangeably with a "stable liquid pharmaceutical preparation."

The composition according to the present disclosure comprises (A) a mixture of two or more different anti-influenza virus antibodies or antigen-binding fragments thereof; (B) a surfactant; (C) sugar or a sugar derivative; and (D) an amino acid.

In addition, the present disclosure provides a pharmaceutical composition for treating influenza virus-related diseases comprising a mixture of two or more different anti-influenza virus antibodies or antigen-binding fragments thereof, by intravenously administering a mixture of the antibody or the antigen-binding fragments thereof at a dose of 10 to 120 mg/kg.

As used herein, the term "not comprise" means not comprising the corresponding component at all. In addition, the relevant term means not substantially comprising the component, i.e., comprising the component in a range that does not affect the activity of the antibody, the stability and viscosity of the liquid pharmaceutical preparation, for example, comprising 0 to 1% (w/v), 0 to 1 ppm (w/v), or 0 to 1 ppb (w/v), based on the total weight of the liquid pharmaceutical preparation.

The composition comprising a mixture of two or more different anti-influenza virus antibodies or antigen-binding fragments thereof according to the present disclosure may be respectively formulated in the oral dosage form of powders, granules, tablets, capsules, suspensions, emulsions, syrups, aerosols, etc., a form of an external preparation, a sterile injection solution for suppositories, or a pre-filled syringe solution, or a lyophilized form, according to conventional method. In detail, in the case of formulation, it may be prepared using diluents or excipients such as fillers, extenders, binders, wetting agents, disintegrants, and surfactants, etc, which are conventionally used. Solid formulation for oral administration includes tablets, pills, powders, granules, capsules, etc., and these solid formulations may be prepared by mixing at least one excipient, for example, starch, calcium carbonate, sucrose, lactose, gelatin, etc., with the extracts. Also, in addition to simple excipients, lubricants such as magnesium stearate and talc may be used. A liquid formulation for oral administration may be suspensions, oral liquids, emulsions, syrups, etc., and include various excipients, for example, wetting agents, sweeteners, aromatics, preservatives, etc., in addition to water and liquid paraffin which are simple diluents commonly used. Formulation for parenteral administration includes sterilized aqueous solutions, non-aqueous solutions, suspensions, emulsions, lyophilized formulations, and suppositories. As the non-aqueous solvent and suspending agent, propylene glycol, polyethylene glycol, vegetable oil such as olive oil, and injectable ester such as ethyl oleate may be used. As a base for suppositories, witepsol, macrogol, tween 61, cacao butter, laurin butter, glycerogelatin, etc., may be used.

(A) Antibody or Antigen-Binding Fragment Thereof

In one embodiment, the composition according to the present disclosure may comprise a mixture of two or more different anti-influenza virus antibodies of the present disclosure, or antigen-binding fragments thereof as described above.

The concentration of the mixture of antibodies or antigen-binding fragments thereof may be freely adjusted within a range that does not substantially adversely affect the stability and viscosity of the composition according to the present disclosure.

In one embodiment of the present disclosure, the concentration of a mixture of antibodies or antigen-binding fragments thereof may be a dose of 5 to 200 mg/mL. In another embodiment of the present disclosure, the concentration may be 10 to 120 mg/mL. In another embodiment of the present disclosure, the concentration may be 20 to 100 mg/mL. When the concentration is within this range, long-term stability may be excellent. The concentration may be freely adjusted within a range that does not substantially adversely affect the stability of the liquid pharmaceutical formulation according to the present disclosure.

(B) Surfactants

In the present disclosure, examples of the "surfactant" include, but are not limited to, polyoxyethylene sorbitan fatty acid ester (e.g., polysorbate), polyoxyethylene alkyl ether (e.g., Brij), alkylphenylpolyoxyethylene ether (for example, Triton-X), polyoxyethylene-polyoxypropylene copolymer (e.g., Poloxamer, Pluronic), sodium dodecyl sulfate (SDS), etc.

In one embodiment of the present disclosure, the surfactant may include polysorbate, poloxamer, or a mixture thereof. In another embodiment of the present disclosure, the surfactant may include polysorbate 20, polysorbate 40, polysorbate 60, polysorbate 80, or a mixture of two or more thereof. In another embodiment of the present disclosure, the surfactant may include polysorbate 80.

In one embodiment of the present disclosure, the concentration of the surfactant may be 0.001 to 10% (w/v). In another embodiment of the present disclosure, the concentration may be 0.01 to 1.0% (w/v). In another embodiment of the present disclosure, the concentration may be 0.05 to 0.5% (w/v).

When the concentration is within this range, the composition according to the present disclosure may be excellent in terms of stability. The concentration may be freely adjusted within a range that does not substantially adversely affect the stability of the liquid pharmaceutical formulation according to the present disclosure.

(C) Sugar or Sugar Derivative

The "sugar" in the present disclosure may include a monosaccharide, a disaccharide, an oligosaccharide, a polysaccharide, or a mixture of two or more thereof. Examples of monosaccharides include, but are not limited to, glucose, fructose, galactose, etc. Examples of disaccharides include, but are not limited to, sucrose, lactose, maltose, trehalose, etc. Examples of oligosaccharides include, but are not limited to, fructooligosaccharides, galactooligosaccharides, mannan oligosaccharides, etc. Examples of polysaccharides include, but are not limited to, starch, glycogen, cellulose, chitin, pectin, etc.

In the present disclosure, the "sugar derivative" may include a sugar alcohol, a sugar acid, or a mixture thereof. Examples of sugar alcohols include, but are not limited to, glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol, polyglycitol, etc. Examples of sugar acids include, but are not limited to, aldonic acid (glyceric acid, etc.), ulosonic acid (neuraminic acid, etc.), uronic acid (glucuronic acid, etc.), aldaric acid (tartaric acid, etc.), or the like.

In one embodiment of the present disclosure, the sugar may include a monosaccharide, a disaccharide, an oligosaccharide, a polysaccharide, or a mixture of two or more thereof, and the sugar derivative may include a sugar alcohol, a sugar acid, or a mixture thereof. In one embodiment of the present disclosure, the sugar or the sugar derivative may include sorbitol, mannitol, trehalose, sucrose, or a mixture of two or more thereof.

In one embodiment of the present disclosure, the concentration of the sugar or the sugar derivative may be 0.01 to 30% (w/v). In another embodiment of the present disclosure, the concentration may be 0.1 to 15% (w/v). In another embodiment of the present disclosure, the concentration may be 1.0 to 10% (w/v). When the concentration is within this range, the composition according to the present disclosure may be excellent in terms of stability. The concentration may be freely adjusted within a range that does not substantially adversely affect the stability of the liquid pharmaceutical formulation according to the present disclosure.

(D) Amino Acid

In the present disclosure, the "amino acid" may include a free amino acid, a salt of amino acid, or a mixture thereof. The free amino acid refers to a free amino acid that does not perform peptide bonds between amino acids, or ester bonds between amino acids and other molecules. Examples of amino acids include, but are not limited to, aspartic acid, histidine, lysine, arginine, etc. Examples of a salt of amino acid include, but are not limited to, a salt of aspartic acid, a salt of histidine, a salt of lysine, and a salt of arginine, etc.

In one embodiment of the present disclosure, the amino acid may include aspartic acid, histidine, lysine, arginine or salt thereof. In another embodiment of the present disclosure, the amino acid may include histidine, a salt of the histidine or a mixture thereof.

In another embodiment of the present disclosure, the amino acid may include a mixture of histidine and histidine-HCl.

In one embodiment of the present disclosure, the amino acid may include a free amino acid, a salt of amino acid, or a mixture thereof.

In another embodiment of the present disclosure, the amino acid may be a buffer.

The "buffer" refers to a neutralizing material that minimizes a change in pH due to an acid or an alkali, and refers to a material that maintains a pH in a specific range without a pH adjuster.

In one embodiment of the present disclosure, the concentration of the amino acid may be 0.1 to 40 mM. In another embodiment of the present disclosure, the concentration may be 1 to 20 mM. In another embodiment of the present disclosure, the concentration may be 5 to 15 mM. When the concentration is within this range, the composition according to the present disclosure may be excellent in terms of stability. The concentration may be freely adjusted within a range that does not substantially adversely affect the stability of the liquid pharmaceutical formulation according to the present disclosure.

(E) pH

The pH of a stable liquid pharmaceutical formulation in the present disclosure may be 5.5 to 6.5. When the pH is within this range, long-term stability may be excellent. The pH may be adjusted using buffers or amino acids. In other words, when buffers or amino acids are included in a small amount, the pH within the above range may be maintained without a separate pH adjuster.

In another embodiment of the present disclosure, the pH may be adjusted with an additional pH adjuster. The pH adjuster may be an acid or a base (e.g., sodium hydroxide), but is not limited thereto.

(F) Other Ingredients

A composition comprising a mixture of two or more different anti-influenza virus antibodies or antigen-binding fragments thereof of the present disclosure may comprise additionally additives known in the art within a range that does not substantially adversely affect the activity of the antibody and the stability of the formulation.

In another embodiment of the present disclosure, examples of the additive may include, but are not limited to, an additional buffer, a diluent, a solubilizing agent, a pH adjuster, a sedative agent, another inorganic or organic salt, an antioxidant, an aqueous carrier, or a mixture thereof. In another embodiment of the present disclosure, an aqueous carrier, an antioxidant, or a mixture of two or more thereof may be further included. Aqueous carriers are pharmaceutically acceptable (safe and non-toxic when administered to humans) and may include carriers useful in the preparation of the liquid pharmaceutical formulations of the present disclosure.

(G) "Stable" Liquid Pharmaceutical Formulation

The term "stable" in the "stable" liquid pharmaceutical formulation of the present disclosure means that the antibody according to the present disclosure substantially retains physical stability and/or chemical stability and/or biological activity thereof during the preparation process and/or upon storage. Various analytical techniques for measuring the stability of an antibody are readily available in the art.

In the present disclosure, "physical stability" may be evaluated by a method known in the art, and such a method may include measuring the apparent attenuation of a sample of light (absorption or optical density). This measurement of light attenuation is related to the turbidity of the formulation. In addition, the content of high molecular weight of component, the content of the low molecular weight of component, the amount of intact protein, and the number of insoluble foreign particles may be measured for physical stability.

In the present disclosure, "chemical stability" may be evaluated by a method known in the art, and such a method may include an evaluation to detect and quantify an antibody in a chemically modified form. In addition, the charge variant (e.g., generated as a result of deamidation or oxidation), etc., may be measured using ion exchange chromatography in relation with chemical stability. The charge variant may be measured using the ion exchange chromatography through an acidic or basic peak.

In the present disclosure, "storage stability" means that the antibody substantially retains biological activity, for example, during transportation, even in the case of altered climatic conditions, an environment of elevated temperature and atmospheric humidity, an environment in which shear stress is applied, etc. The storage stability may be measured through various assays measuring the biological activity of the antibody in a long-term elevated temperature and atmospheric humidity environment.

In the present disclosure, "biological activity" may be evaluated by a method known in the art, and such a method may include measuring antigen binding affinity through Enzyme Linked Immuno Sorbent Assay (ELISA).

In one embodiment of the present disclosure, a liquid pharmaceutical formulation may be stable for a long period of time.

In one embodiment of the present disclosure, the term "stable" liquid pharmaceutical formulation refers to a liquid pharmaceutical formulation that satisfies one or more of the following.

Appearance Analysis

A liquid pharmaceutical formulation that maintains a degree of transparency in appearance after storage for 6 weeks in a temperature 40±2° C., relative humidity 75±5%, and closed conditions;

A liquid pharmaceutical formulation that maintains the degree of transparency in appearance after storage for 12 months in a temperature 5±3° C., ambient humidity, and closed conditions;

pH

A liquid pharmaceutical formulation that satisfies 6.0±0.5 as a result of measuring pH after storage for 12 months in a temperature 5±3° C., ambient humidity, and closed conditions;

Asepsis

A liquid pharmaceutical formulation that prevents a growth of the microorganism of the media in isolator after storage for 12 months in a temperature 5±3° C., ambient humidity, and closed conditions;

Concentration of Antibody

A liquid pharmaceutical formulation wherein the concentration of a single antibody measured by HIC-HPLC after storage for 6 weeks at a temperature of 5±3° C., ambient humidity, and closed conditions is 50±5.0 mg/mL, or each concentration of the single antibodies constituting the antibody mixture is 25±2.5 mg/mL and a concentration of an antibody mixture is 50±5.0 mg/mL;

A liquid pharmaceutical formulation wherein the concentration of a single antibody measured by HIC-HPLC after storage for 6 weeks at a temperature of 25±2° C., relative humidity 60±5%, and closed conditions is 50±5.0 mg/mL, or each concentration of the single antibodies constituting the antibody mixture is 25±2.5 mg/mL and a concentration of an antibody mixture is 50±5.0 mg/mL;

A liquid pharmaceutical formulation wherein the concentration of a single antibody measured by HIC-HPLC after storage for 6 weeks at a temperature of 40±2° C., relative humidity 75±5%, and closed conditions is 50±5.0 mg/mL, or each concentration of the single antibodies constituting the antibody mixture is 25±2.5 mg/mL and a concentration of an antibody mixture is 50±5.0 mg/mL;

A liquid pharmaceutical formulation wherein the concentration of a single antibody measured by HIC-HPLC after storage for 12 months at a temperature of 5±3° C., ambient humidity, and closed conditions is 50±5.0 mg/mL, or each concentration of the single antibodies constituting the antibody mixture is 25±2.5 mg/mL and a concentration of an antibody mixture is 50±5.0 mg/mL;

Content of Intact Immunoglobulin G (Intact IgG %)

A liquid pharmaceutical formulation wherein the content of intact immunoglobulin G (Intact IgG %) measured by Chip-based CE-SDS after storage for 6 weeks at a temperature of 40±2° C., relative humidity 75±5%, and closed conditions is 95.0 to 100%;

A liquid pharmaceutical formulation wherein the content of intact immunoglobulin G (Intact IgG %) measured by non-reducing CE-SDS after storage for 12 months at a temperature of 5±3° C., ambient humidity, and closed conditions is 90.0 to 100%;

The Content of Intact Heavy Chain and Light Chain (Intact HC+LC %)

A liquid pharmaceutical formulation wherein the content of intact light chain and heavy chain (Intact HC+LC %) measured by reducing CE-SDS after storage for 12 months at a temperature of 5±3° C., ambient humidity, and closed conditions is 95.0 to 100%;

Content of Antibody Monomer

A liquid pharmaceutical formulation wherein the content of antibody monomer measured by SEC-HPLC after storage for 6 weeks at a temperature of 40±2° C., relative humidity 75±5%, and closed conditions is 95.0 to 100%;

A liquid pharmaceutical formulation wherein the content of antibody monomer measured by SEC-HPLC after storage for 12 months at a temperature of 5±3° C., ambient humidity, and closed conditions is 95.0 to 100%;

Binding Affinity of HA to Influenza a Virus

A liquid pharmaceutical formulation wherein binding affinity of HA measured by Cellular Enzyme-Linked Immunosorbent assay (CELISA) or ELISA after storage for 6 weeks at a temperature of 5±3° C., ambient humidity, and closed conditions is 70 to 130%;

A liquid pharmaceutical formulation wherein binding affinity of HA measured by Cellular Enzyme-Linked Immunosorbent assay (CELISA) or ELISA after storage for 6 weeks at a temperature of 25±2° C., relative humidity 60±5%, and closed conditions is 70 to 130%;

A liquid pharmaceutical formulation wherein binding affinity of HA measured by Cellular Enzyme-Linked Immunosorbent assay (CELISA) or ELISA after storage for 6 weeks at a temperature of 40±2° C., relative humidity 75±5%, and closed conditions is 70 to 130%;

A liquid pharmaceutical formulation wherein binding affinity of HA measured by Cellular Enzyme-Linked Immunosorbent assay (CELISA) or ELISA after storage for 12 months at a temperature of 5±3° C., ambient humidity, and closed conditions is 70 to 130%;

(H) Method for Preparing Stable Liquid Pharmaceutical Formulation

The stable liquid pharmaceutical formulation of the present disclosure may be prepared by using a known method, but is not limited to a specific method.

In one embodiment of the present disclosure, the preparation method may be a method for preparing a stable liquid pharmaceutical formulation, said method comprising: i) preparing a mixed solution wherein an amino acid is added to the solution containing sugar or a sugar derivative; ii) preparing a mixed solution containing the antibody or antigen-binding fragment thereof by exchanging a buffer between the mixed solution of step i) and a solution containing a mixture of the antibody or the antigen-binding fragment thereof, and iii) adding a solution containing a surfactant to the mixed solution containing the antibody or the antigen-binding fragment thereof of step ii).

In one embodiment of the present disclosure, a method for preparing a stable liquid pharmaceutical formulation comprising a mixture of two or more different anti-influenza virus antibodies or antigen-binding fragments thereof is possible to prepare a stable liquid pharmaceutical formulation by the preparation method above after mixing antibodies or antigen-binding fragments thereof or preparing their mixture.

In one embodiment of the present disclosure, the preparation method may not include a freeze-drying process or may include a freeze-drying process upon the preparation.

In another embodiment of the present disclosure, when the preparation method does not comprise a freeze-drying process, the preparation method may further include preparing a liquid pharmaceutical formulation and placing the liquid pharmaceutical formulation in a closed container immediately after treatment such as sterilization, etc.

In another embodiment of the present disclosure, when the preparation method includes a freeze-drying process, the preparation method further includes replenishing or replacing components that have been removed or modified by being lyophilized and/or stored after the liquid pharmaceutical formulation is prepared and lyophilized, or after the liquid pharmaceutical formulation of the present disclosure is prepared, lyophilized, and stored. In addition, the preparation method may include adding the components that have been excluded, after lyophilizing and storing only the components excluding components that may be removed or modified by being lyophilized and/or stored, or after lyophilizing and storing only the components excluding components that may be removed or modified by being lyophilized and/or stored in the liquid pharmaceutical formulation of the present disclosure.

Use of Stable Liquid Pharmaceutical Formulation

The stable liquid pharmaceutical formulation of the present disclosure may be used for diagnosis, prevention, or treatment of influenza virus infection. In one embodiment of the present disclosure, the stable liquid pharmaceutical formulation of the present disclosure may be used for diagnosis, prevention, or treatment of diseases caused by influenza virus infection. In another embodiment of the present disclosure, diseases caused by influenza virus infection include, but are not limited to, pneumonia, otitis media, etc.

In one embodiment of the present disclosure, the stable liquid pharmaceutical formulation may be for intravenous, intramuscular, intradermal, subcutaneous, intraperitoneal, topical administration, or a combination thereof.

In one embodiment of the present disclosure, the stable liquid pharmaceutical formulation may be used for single or multiple administration.

In one embodiment of the present disclosure, the concentration of the antibody and other components in the liquid pharmaceutical formulation is as described above, and the total volume of the liquid pharmaceutical formulation may be 0.1 to 100 mL.

The dosage and timing of administration of the liquid pharmaceutical formulation of the present disclosure may vary depending on the type of disease, the severity and course of the disease, the patient's health and response to treatment, and the judgment of the treating doctor, and are not limited to the specific dosage and timing of administration.

Diagnosis, Prevention, or Treatment Method

The present disclosure provides a method for diagnosis, prevention or treatment of influenza virus, comprising administering the composition comprising a mixture of two or more different anti-influenza virus antibodies or antigen-binding fragments thereof to a patient, wherein the composition comprises (A) a mixture of two or more different anti-influenza virus antibodies or antigen-binding fragments thereof, (B) a surfactant; (C) sugar or a sugar derivative; and (D) an amino acid.

In addition, the present disclosure provides use of the mixture of two or more different anti-influenza virus antibodies or antigen binding fragments thereof, in the preparation of a pharmaceutical composition for treating influenza virus-related diseases by administering a mixture of two or more different anti-influenza virus antibodies or antigen binding fragments thereof to a patient, wherein the mixture of anti-influenza virus antibodies or antigen-binding fragments thereof is administered at a dose of 10 to 120 mg/kg.

In one embodiment of the present disclosure, the method for prevention or treatment method may be applied with a therapeutic agent known to those skilled in the art. In another embodiment of the present disclosure, the method for the prevention or treatment may further comprise co-administering an anti-viral drug.

In another embodiment of the present disclosure, examples of the anti-viral drug may include, but are not limited to, an anti-influenza virus monoclonal antibody, an anti-influenza virus polyclonal antibody, a DNA polymerase inhibitor, a siRNA agent, or a therapeutic vaccine.

Stabilization Method

The present disclosure provides a method for stabilizing the antibody within the liquid pharmaceutical formulation, comprising preparing a stable liquid pharmaceutical formulation comprising (A) a mixture of two or more different anti-influenza virus antibodies or antigen-binding fragments thereof; (B) a surfactant; (C) sugar or a sugar derivative; and (D) an amino acid.

Kit

The present disclosure provides a kit comprising a stable liquid pharmaceutical formulation comprising (A) an anti-influenza virus antibody or a mixture of two or more different anti-influenza virus antibodies; (B) a surfactant; (C) sugar or a sugar derivative and (D) an amino acid; and a container containing the stable liquid pharmaceutical formulation in a closed state.

In addition, the present disclosure provides a kit comprising (a) a composition comprising a mixture of two or more different anti-influenza virus antibodies or antigen-binding fragments thereof; and (b) instructions directed for administering a mixture of the antibody or antigen-binding fragment thereof at a dose of 10 to 120 mg/kg to treat a patient with an influenza virus-related disease.

In one embodiment of the present disclosure, the container may be formed from a material such as glass, polymer (plastic), or metal, etc., but is not limited thereto. In one embodiment of the present disclosure, the container is a bottle, vial, syringe, or tube, but is not limited thereto.

In one embodiment of the present disclosure, the container may be a glass or polymer vial, or a glass or polymer pre-filled syringe.

In one embodiment of the present disclosure, the inside of the container may not be coated with silicone oil. If silicone oil is coated, stability may be deteriorated. The container may be a container for single administration or multiple administrations.

Specific product types such as the vial, cartridge, pre-filled syringe, auto-injector, and the method of filling the stable liquid pharmaceutical formulation into the vial, cartridge, pre-filled syringe, auto-injector, etc. may be easily obtained or carried out generally by those skilled in the art in the technical field to which the present disclosure belongs. For example, U.S. Pat. Nos. 4,861,335 and 6,331,174 etc., disclose specific product types of pre-filled syringes and methods of filling thereto. For example, U.S. Pat. Nos. 5,085,642, 5,681,291, etc., disclose specific product types of auto-injectors and its assembly methods. As the vial, cartridge, pre-filled syringe, auto-injector, etc., a commercially available product may be used as it is, or a separately custom-made product may be used in consideration of the physical properties, administration site, and dosage of the stable liquid pharmaceutical formulation.

In one embodiment of the present disclosure, the kit may further include instructions for providing a method of using the stable liquid pharmaceutical formulation, a storage method of the formulation, or all methods. The method for use may include a method of diagnosis, prevention, or treatment of an influenza virus infection, and may include an administration route, dosage, and timing of administration.

In one embodiment of the present disclosure, the kit may include other tools required in terms of a commercial and user perspective. In another embodiment of the present disclosure, the other tools may include a needle, a syringe, etc.

In one embodiment of the present disclosure, the kit may additionally include a pharmaceutically acceptable excipient, and the pharmaceutically acceptable excipient refers to an inert material to be combined with an active molecule such as an antibody for preparing an acceptable or convenient dosage form. The pharmaceutically acceptable excipient is an excipient that is non-toxic to the recipient at the dosages and concentrations used and is compatible with the other components of the composition comprising the monoclonal antibody.

Hereinafter, the present disclosure will be described in detail according to examples. However, the following examples are presented only to illustrate the content of the present disclosure, and the scope of the present disclosure is not limited by the examples. Documents cited in the present disclosure and Korean Patent Application No. 10-2011-0020061, Korean Patent Application No. 10-2012-0107512, Korean Patent Application No. 10-2014-0036601, and Korean Patent Application No. 10-2017-0100975 previously filed by the present applicant, are incorporated by reference herein.

Example 1. Evaluation of Safety and Therapeutic Efficacy Upon Single Administration of Anti-Influenza Virus Antibody Mixture (Intravenous Administration) in Flu Patients In this clinical trial, after preparing an antibody mixture of 1:1 ratio of anti-influenza virus antibodies CT-P22 and CT-P23 (referred to as CT-P27 in the present disclosure), this is a randomized, double-blind, multicenter, placebo-controlled phase 2b trial designed to evaluate the efficacy and safety of this CT-P27 in infected subjects of acute influenza A (virus) infection without complications.

Patients must meet all of the following criteria in order to be enrolled in this clinical trial.

1. Male or female subjects aged 19-64 years.
2. Subjects who can voluntarily provide written consent.
3. Subjects who developed disease within 48 hours prior to administration of the test drug. If the visit schedule needs adjustment, additional 12 hours are acceptable (maximum disease onset time: within 60 hours)
  ※ Precautions: Disease onset time is defined as the earliest time point in (a) and (b): (a) At the time that the body temperature was first measured above 38.0° C. (100.4° F.) or
  (b) At the time of that at least two respiratory or systemic symptoms in the subject (moderate to severe intensity) are developed.
4. Based on the Flu-iiQ™ record reported and written by the subject at screening, subjects with at least two of the following symptoms (moderate to severe intensity):
  (a) Respiratory symptoms (cough, sore throat, or stuffy nose) or
  (b) Systemic symptoms (headache, fever, throb with pain all over the body, or fatigue).
5. Subjects with high fever of 38.0° C. (100.4° F.) or more at screening, or high fever within 24 hours before screening, but receiving antipyretic treatment within 6 hours before screening.
6. Subjects who have been diagnosed with influenza A using a rapid influenza diagnostic test provided by the customer or previously negotiated at the time of screening. If there is a result of being diagnosed with influenza A prior to signing the consent form, and the result is obtained from a rapid influenza diagnosis test previously discussed with the customer, the result can be used.

7. In both male and female subjects, if the subjects and their partner (possibly conceived) agree to use highly effective contraception during the study period and for 5 months after administration of the test drug.
   a) Male and female subjects and their partners whose duration of surgical sterilization is less than 6 months prior to the date of consent of the subject must agree to use effective contraception during the study period and for 5 months after administration of the test drug.
   b) Menopausal women who are subject to the last menstruation to be classified as non-fertile Subjects must have experienced 12 months prior to the date of consent 8. Subjects whose body mass index is less than 35 kg/m² and their weight is less than 99.9 kg.

In addition, patients could not be enrolled in this clinical trial if they met any of the following criteria.

1. Anyone who may not complete all necessary test visits or procedures at the discretion of the investigator.
2. Anyone who has been treated with drug for clinical trials or participated in other clinical trials within 30 days (or 5-fold half-life, based on a longer period).
3. Anyone who has been exposed to anti-influenza monoclonal antibody, including CT-P27, prior to administration of the test drug.
4. Anyone with a history of hypersensitivity to monoclonal antibodies or with known hypersensitivity to therapeutic components.
5. Anyone who is receiving antiviral treatment for influenza (e.g., zanamivir, oseltamivir, rimantadine, amantadine, laninamivir, peramivir, or ribavirin) or has a history of administration of such antiviral agents within 14 days prior to administration of the test drug.
6. Anyone who received live attenuated vaccine or inactivated virus vaccine against influenza within 21 days prior to administration of the test drug.
7. Anyone with a medical condition that includes one or more of the following:
   a) In the case of showing positive response for influenza B infection or positive response for influenza A+B infection.
   b) Past or current history of congestive heart failure with symptoms consistent with New York Heart Association Grade III or IV functional status within 12 months prior to administration of the test drug.
   c) In the case of showing a clinically significant abnormal result on the 12-guided ECG during the screening test, and interfering with the subject's safety or affecting the test result according to the clinical judgment of the investigator.
   ※ This includes, but is not limited to, the following: PR interval >200 msec, calibrated QT interval [QTc]>450 msec (male) and >470 msec (female), or all evidences of heart block, right bundle branch block, or left bundle branch block).
   d) Anyone with a past or current history of clinical condition or organ dysfunction that is judged to affect the test subject's ability to participate in the test, or the test result at the discretion of the investigator.
   e) Anyone with abnormal results in liver function tests. In screening, the cases that serum aspartate transaminase (AST) values are 3 times or more the ULN, serum alanine transaminase (ALT) values are 3 times or more the ULN or alkaline phosphatase (ALP) value is 3 times or more the ULN are included.
   f) Anyone with abnormal results in renal function tests. In the screening, the cases that the serum creatinine value is 1.7 times or more the ULN and the creatinine clearance rate is 75 mL/min or less, are included.
   g) Anyone with active tuberculosis in the judgment of the investigator.
   h) Uncontrolled diabetes (defined as a case known as glycated hemoglobin (HbA1C) >8%).
   i) Uncontrolled hypertension (defined as a case known as systolic blood pressure (SBP) ≥160 mmHg or diastolic blood pressure (DBP) ≥100 mmHg).
   j) Anyone who is currently infected with hepatitis B, hepatitis C, or human immunodeficiency virus (HIV) and has a record.
   k) Anyone with severe infection, who requires parenteral antibiotic use or hospitalization within 30 days prior to administration of the test drug.
   l) Patients with uncontrolled, clinically significant acute or chronic respiratory disease (e.g., chronic obstructive pulmonary disease, cystic fibrosis, bronchiectasis, asthma, or bacterial pneumonia).
   m) Patients with a past history of malignant tumor within 2 years prior to administration of the test drug (excluding basal cell carcinoma of the treated skin or superficial cervical cancer) or currently active malignant tumor.
8. Subjects who are currently hospitalized or need to be hospitalized due to the severity of the disease, or who have an optional hospitalization plan within 1 month after administration of the test drug.
9. Subjects requiring oxygen therapy due to underlying disease or influenza infection.
10. Anyone who has undergone a bone marrow transplant or a substantial organ transplant.
11. Anyone who has used systemic steroids or other immunosuppressants (excluding oral steroids up to 5-10 mg/day, methotrexate up to 10 mg/week).
12. Subjects requiring regular/intermittent hemodialysis or peritoneal dialysis.
13. Subjects who are pregnant or breastfeeding.
14. At the discretion of the investigator, the cases that the written consent may be invalidated due to an incompatibility for participation in the clinical trial by diagnostic test results and other reasons, psychological and emotional problems, disabilities, or the resulting treatment status, or there is a limitation in complying with the clinical trial protocol, or anyone who cannot understand the requirements, instructions, limitations, nature, scope, and possible outcomes of the clinical trial protocol. Alternatively, anyone who are unable to provide the written consent or who cannot fully follow the clinical trial protocol.

This clinical trial consisted of three clinical trial periods: screening, dosing, and after dosing. Subjects received a rapid influenza diagnostic test within 24 hours before treatment with the test drug, and in order to be eligible for registration, the rapid diagnostic test result for influenza A virus had to be positive. The presence of influenza A virus was confirmed by quantitative polymerase chain reaction (qPCR) and cell culture in only registered subjects. As a result of the rapid diagnostic test, subjects who were positive for influenza A virus, but negative for qPCR or cell culture, were subject to the continued test and were followed up for safety purposes.

A total of 228 subjects enrolled in this trial were randomized to one of the three groups: CT-P27 at 90 mg/kg, CT-P27 at 45 mg/kg, or placebo. Randomization was stratified according to the influenza vaccination history within 1 year (Yes or No) and participation in the sub-clinical trial of pharmacokinetics (Yes or No). All enrolled subjects received a single dose of 90 mg/kg CT-P27, 45 mg/kg CT-P27, or placebo intravenously for 90 minutes (±15 minutes) on Day 1. In addition, a pharmacokinetic subtest was conducted with a total of 58 subjects who signed the written consent to participate in the pharmacokinetic subtest (Table 1).

TABLE 1

| Analysis group | Group of subjects | | | |
|---|---|---|---|---|
| | CT-P27 90 mg/kg | CT-P27 45 mg/kg | Placebo group | Total |
| Group having treatment intention [1] | 88 | 90 | 50 | 228 |
| Infectious group having treatment intention [2] | 87 | 86 | 48 | 221 |
| Safety group [3] | 88 | 90 | 50 | 228 |
| Pharmacokinetic group [4] | 19 | 22 | 17 | 58 |

[1] Group having treatment intention: All subjects randomly assigned to test drug or placebo,
[2] Infectious group having treatment intention: All randomized subjects with confirmed influenza A by qPCR or cell culture
[3] Safety group: All randomized subjects who received any part of the test drug or placebo
[4] Pharmacokinetic group: All randomized subjects who had the influenza A confirmed by qPCR or cell culture, and were administered with the full dose of the test drug and had at least one PK sample after administration Subjects were admitted to the laboratory at predefined time intervals for clinical evaluation, nasopharyngeal smear collection, and blood collection. In addition, the subjects recorded the Flu-iiQ™ questionnaire, body temperature, adverse reactions, and concomitant drugs in their diaries from $1^{st}$ to $8^{th}$. The clinical trial termination visit was conducted on Day 110, but the subjects who terminated the trial early conducted the clinical trial termination visit to evaluate safety variables at any time (Table 2).

TABLE 2

Record items and schedule of subjects

| Evaluation | Screening | Treatment Day 1 | Day 2 | Day 3 | Day 5 | Day 8 | After the treatment | | | |
|---|---|---|---|---|---|---|---|---|---|---|
| | | | | | | | Day 15 (±2 day) | Day 29 (±5 day) | Day 57 (±5 day) | Day 110/EOS visit (±5 day) |
| Consent by subjects | X | | | | | | | | | |
| Demographic information, medical history, height | X | | | | | | | | | |
| Selection/Exclusion Criteria | X | | | | | | | | | |
| Physical examination and weight | X | | | | | | | | | X |
| Hepatitis B/C and HIV test (test institution) | X | | | | | | | | | |
| Urine pregnancy test (test institution) | X | | | | | | | | | X |
| Diagnostic test (test institution) | X | | | X | | X | | | | |
| Vital signs (blood pressure, heart rate, respiratory rate) | X | X | X | X | X | X | | | | X |
| 12-induction ECG | X | | | | | X | | | | X |
| Chest x-ray | X | | | (X) | | | | | | |
| Randomization | | X | | | | | | | | |
| CT-P27 or placebo administration | | X | | | | | | | | |
| PK blood collection (subgroup [PK] cohort only) | | X | X | X | | X | X | X | X | X |
| Immunogenic blood collection | | X | | | | | | | | X |
| Blood collection for HI antibody (subgroup [PK] cohort only) | | X | | | | | | X | | |
| Monitoring for immediate hypersensitivity | | X | | | | | | | | |

TABLE 2-continued

Record items and schedule of subjects

| | | | | | | After the treatment | | | |
|---|---|---|---|---|---|---|---|---|---|
| Evaluation | Screening | Treatment Day 1 | Day 2 | Day 3 | Day 5 | Day 8 | Day 15 (±2 day) | Day 29 (±5 day) | Day 57 (±5 day) | Day 110/EOS visit (±5 day) |
| Collection of nasopharyngeal smear | X | | X | X | X | X | | | | |
| Rapid influenza diagnostic test | X | | | | | | | | | |
| Virus titer (qPCR and cell culture) | X | | X | X | X | X | | | | |
| Characterization of isolated influenza virus | X | | | (X) | | | | | | |
| Doctor evaluation | X | | X | X | X | X | | | | X |
| Flu-iiQ ™ | X | | | X | | | | | | |
| Body temperature | X | X | X | X | X | X | | | | X |
| Concomitant drug | X | X (Continuously throughout entire test period) | | | | | | | | |
| Adverse reactions | X | X (Continuously throughout entire test period) | | | | | | | | |

Result 1-1. Safety Evaluation

Safety evaluation is a secondary evaluation variable of clinical trials, and items such as adverse events (including serious adverse events), diagnostic tests (hematology, biochemistry, urine analysis), vital signs measurement (blood pressure, heart rate and respiratory rate, body temperature), monitoring for hypersensitivity reaction, and electrocardiogram (ECG) test, physical examination findings, body weight, pregnancy test, chest X-ray test, evaluation of suspected ADE, and immunogenicity evaluation were conducted for the safety.

(i) Summary of Adverse Events

The cumulative safety data of this study included data up to Day 110/EOS for patients enrolled in 2016-2017 and up to Day 15 for enrolled patients in 2017-2018 and overall summary for adverse events was indicated in Table 3. Overall, 113 adverse events occurred after treatment occurred in 68 (29.8%) patients. The severity of adverse events that occurred after most treatments was represented as grade 1 or grade 2, and there were no grades 4 or 5.

Among the adverse events after all treatment, 7 patients (8.0%) in the 90 mg/kg CT-P27 group, 5 patients (5.6%) in the 45 mg/kg CT-P27 group, and 3 patients (6.0%) in the placebo group were considered that the adverse events occurred in the case were related to the present drug.

A serious adverse event occurred after treatment occurred in 1 patient. This occurred in the 90 mg/kg of CT-P27 administration group, and the investigator considered this adverse event to be due to pneumonia and not related to the present drug.

Among adverse events after treatment, infusion-related reactions or anaphylaxis were found in 5 patients (5.7%) in the 90 mg/kg of CT-P27 group, 2 patients (2.2%) in the 45 mg/kg of CT-P27 group, and 1 patient (2.0%) in the placebo group. Among a total of 8 cases, the intensity of 7 adverse events was grade 1, and one event was grade 2. There were no infusion-related reactions or discontinuation due to anaphylaxis in adverse events, and all patients were recovered.

There were no cases of discontinuation of an administration of the present drug, or death due to adverse events that occurred after treatment.

TABLE 3

Summary of adverse events after treatment

| Result | CT-P27 90 mg/kg N = 88 n (%) | CT-P27 45 mg/kg N = 90 n (%) | Placebo N = 50 n (%) | Total N = 228 n (%) |
|---|---|---|---|---|
| Number of adverse events (case) | 35 | 48 | 31 | 114 |
| Number of patients who experienced at least one adverse event (%) | 24 (27.3) | 28 (31.1) | 17 (34.0) | 69 (30.3) |
| Number of adverse events after treatment (case) | 35 | 47 | 31 | 113 |
| Number of patients who experienced adverse events (%) after treatment of at least one case | 24 (27.3) | 27 (30.0) | 17 (34.0) | 68 (29.8) |
| Related | 7 (8.0) | 5 (5.6) | 3 (6.0) | 15 (6.6) |
| Irrelevant | 19 (21.6) | 25 (27.8) | 15 (30.0) | 59 (25.9) |
| Number of severe adverse events (case) | 1 | 0 | 0 | 1 |
| Number of patients who experienced severe adverse events (%) after treatment of at least one case | 1 (1.1) | 0 | 0 | 1 (0.4) |

TABLE 3-continued

Summary of adverse events after treatment

| Result | CT-P27 90 mg/kg N = 88 n (%) | CT-P27 45 mg/kg N = 90 n (%) | Placebo N = 50 n (%) | Total N = 228 n (%) |
|---|---|---|---|---|
| Irrelevant | 1 (1.1) | 0 | 0 | 1 (0.4) |
| Number of patients who discontinued clinical trial drug administration among patients who experienced adverse events after treatment of at least one case (%) | 0 | 0 | 0 | 0 |
| Number of patients who experienced infusion-related reactions or anaphylaxis among patients who experienced adverse events after treatment of at least one case (%) | 5 (5.7) | 2 (2.2) | 1 (2.0) | 8 (3.5) |
| Death case | 0 | 0 | 0 | 0 |

In each summary section, if more than one case was reported, only one case was calculated and only the most severe case was calculated. Each case is judged to be relevant only when the relationship is defined as 'Possible', 'Probable' or 'Definite.'

(ii) Immunogenicity

The immunogenicity results of day 110/EOS included data from patients enrolled in 2016-2017, who completed clinical trials. On day 110/EOS, positive responses of an antibody to the CT-P22 drug (ADA) were observed in only two patients in the 45 mg/kg CT-P27 administration group, and neutralizing antibody (Nab) reactions for both patients were negative. In addition, no drug infusion reactions or hypersensitivity reactions were observed in 2 patients, all influenza symptoms and fever were lost until day 8, and influenza A virus titer was not measured. No patients showed positive antibody (ADA) reaction to the CT-P23 drug (Tables 4 and 5).

TABLE 4

Summary of immunogenicity results for CT-P2

| Result | CT-P27 90 mg/kg N = 88 n (%) | CT-P27 45 mg/kg N = 90 n (%) | Placebo N = 50 n (%) |
|---|---|---|---|
| Before administration of the drug | | | |
| ADA Positive | 2 (2.3) | 5 (5.6) | 2 (4.0) |
| NAb Positive | 0 | 0 | 0 |
| NAb Negative | 2 (2.3) | 5 (5.6) | 2 (4.0) |
| ADA Negative | 85 (96.6) | 84 (93.3) | 47 (94.0) |
| Day 110/EOS | | | |
| ADA Positive | 0 | 2 (2.2) | 0 |
| NAb Positive | 0 | 0 | 0 |
| NAb Negative | 0 | 2 (2.2) | 0 |
| ADA Negative | 13 (14.8) | 12 (13.3) | 8 (16.0) |

TABLE 5

Summary of immunogenicity results for CT-P23

| Result | CT-P27 90 mg/kg N = 88 n (%) | CT-P27 45 mg/kg N = 90 n (%) | Placebo N = 50 n (%) |
|---|---|---|---|
| Before administration of the drug | | | |
| ADA Positive | 4 (4.5) | 4 (4.4) | 1 (2.0) |
| NAb Positive | 0 | 0 | 0 |
| NAb Negative | 4 (4.5) | 4 (4.4) | 1 (2.0) |
| ADA Negative | 83 (94.3) | 85 (94.4) | 48 (96.0) |
| Day 110/EOS | | | |
| ADA Positive | 0 | 0 | 0 |
| NAb Positive | 0 | 0 | 0 |
| NAb Negative | 0 | 0 | 0 |
| ADA Negative | 13 (14.8) | 14 (15.6) | 8 (16.0) |

1-2. Evaluation of Treatment Efficacy
(i) Time to Relieve Influenza Symptoms

If the following influenza symptoms recorded on the Flu-iiQ™ questionnaire were mild or did not appear for at least 24 hours, the symptoms were considered relieved.

Respiratory symptoms: Cough, sore throat, stuffy nose
Systemic symptoms: Headache, fever, throb with pain all over the body, fatigue As a result of the analysis, in the both of 90 mg/kg and 45 mg/kg of CT-P27 groups, the time to relieve influenza symptoms significantly decreased compared to the placebo group (Table 6).

TABLE 6

Statistical results of time to be relieved from influenza symptom in infectious group having treatment intention

| Result | CT-P27 90 mg/kg N = 87 | CT-P27 45 mg/kg N = 86 | Placebo group N = 48 |
|---|---|---|---|
| Relief, n (%) | 62 (71.3) | 65 (75.6) | 24 (50.0) |
| Mid-cut [1], n (%) | 25 (28.7) | 21 (24.4) | 24 (50.0) |
| Early dropout | 1 (1.1) | 1 (1.2) | 3 (6.3) |
| Not relieved until the point of observation | 24 (27.6) | 20 (23.3) | 21 (43.8) |
| Time from medication to solution [2] (days) median [95% confidence interval] | 3.74 [2.72, 4.46] | 3.69 [2.81, 4.25] | 5.65 [3.65, N/A] |

TABLE 6-continued

Statistical results of time to be relieved from influenza symptom in infectious group having treatment intention

| Result | CT-P27 90 mg/kg N = 87 | CT-P27 45 mg/kg N = 86 | Placebo group N = 48 |
|---|---|---|---|
| P-value (Log-rank test) | 0.017 | 0.007 | |
| P-value (Gehans Wilcoxon test) | 0.016 | 0.012 | |

[1] Mid-cut with the last date/time recorded in the subject's diary,
[2] [Starting date of relieving the symptoms/time] − [Starting date of drug administration/time]

(ii) Time to Relieve Influenza Symptoms and Fever (<37.8° C.)

If the following influenza symptoms recorded on the Flu-iiQ™ questionnaire were mild or did not appear for at least 24 hours, the symptoms were considered relieved.

Respiratory symptoms: Cough, sore throat, stuffy nose
Systemic symptoms: Headache, fever, throb with pain all over the body, fatigue In addition, the relief of fever was defined as follows.
If the body temperature is <37.8° C. for at least 24 hours As a result of the analysis, in the both of 90 mg/kg and 45 mg/kg of CT-P27 groups, the time to relieve influenza symptoms and fever (<37.8° C.) significantly decreased compared to the placebo group (Table 7).

TABLE 7

Statistical results for time to relieve influenza symptoms and fever (<37.8° C.) in infectious group having treatment intention

| Result | CT-P27 90 mg/kg N = 87 | CT-P27 45 mg/kg N = 86 | Placebo group N = 48 |
|---|---|---|---|
| Relief, n (%) | 62 (71.3) | 65 (75.6) | 23 (47.9) |
| Mid-cut [1], n (%) | 25 (28.7) | 21 (24.4) | 25 (52.1) |
| Early dropout | 1 (1.1) | 1 (1.2) | 3 (6.3) |
| Not relieved until the point of observation | 24 (27.6) | 20 (23.3) | 22 (45.8) |
| Time from medication to solution [2] (days) median | 3.74 | 3.69 | 5.72 |
| [95% confidence interval] | [2.72, 4.46] | [2.81, 4.25] | [3.65, NA] |
| P-value (Log-rank test) | 0.012 | 0.005 | |
| P-value (Gehans Wilcoxon test) | 0.014 | 0.010 | |

[1] Mid-cut with the last date/time recorded in the subject's diary,
[2] [Starting date of relieving the symptoms/time] − [Starting date of drug administration/time]

The invention claimed is:

1. A method for treating influenza virus-related diseases, comprising administering to a patient a composition comprising a mixture of two or more different anti-influenza virus antibodies or antigen-binding fragments thereof, wherein the mixture of the antibodies or the antigen binding fragments thereof is administered to the patient at a dose of 10 to 120 mg/kg, and wherein the mixture of two or more different anti-influenza virus antibodies or antigen-binding fragments thereof comprises:
   i) antibodies or antigen-binding fragments thereof comprising a light chain variable region comprising a CDR1 region of SEQ ID NO: 1, a CDR2 region of SEQ ID NO: 2, and a CDR3 region of SEQ ID NO: 3, and a heavy chain variable region comprising a CDR1 region of SEQ ID NO: 4, a CDR2 region of SEQ ID NO: 5, and a CDR3 region of SEQ ID NO: 6; and
   ii) antibodies or antigen-binding fragments thereof comprising a light chain variable region comprising a CDR1 region of SEQ ID NO: 7, a CDR2 region of SEQ ID NO: 8, and a CDR3 region of SEQ ID NO: 9, and a heavy chain variable region comprising a CDR1 region of SEQ ID NO: 10, a CDR2 region of SEQ ID NO: 11, and a CDR3 region of SEQ ID NO: 12.

2. The method of claim 1, wherein the mixture of antibodies or antigen-binding fragments thereof is administered to the patient at a dose of 40 to 100 mg/kg.

3. The method of claim 1, wherein the mixture of antibodies or antigen-binding fragments thereof is intravenously administered.

4. The method of claim 1, wherein the mixture of two or more different anti-influenza virus antibodies or antigen-binding fragments thereof comprises:
   i) antibodies or antigen-binding fragments thereof comprising a light chain variable region of the polypeptide sequence of SEQ ID NO 13 and a heavy chain variable region of the polypeptide sequence of SEQ ID NO 14; and
   ii) antibodies or antigen-binding fragments thereof comprising a light chain variable region of the polypeptide sequence of SEQ ID NO: 15 and a heavy chain variable region of the polypeptide sequence of SEQ ID NO: 16.

5. The method of claim 1, wherein the mixture of antibodies or antigen-binding fragments thereof is administered in combination with zanamivir, oseltamivir, laninamivir, peramivir, rimantadine, amantadine, ribavirin, or a mixture thereof.

6. The method of claim 1, wherein the influenza virus-related diseases cause at least one symptom selected from the group consisting of cough, headache, fever, muscle pain, rhinorrhea, nasal congestion, chills, fatigue, weakness, shortness of breath, vomiting, pain, diarrhea, pneumonia, and bronchitis, caused by the influenza virus.

7. The method of claim 1, wherein the composition comprising a mixture of two or more different anti-influenza virus antibodies or antigen-binding fragments thereof comprises (A) a mixture of two or more different anti-influenza virus antibodies or antigen-binding fragments thereof; (B) a surfactant; (C) sugar or a sugar derivative; and (D) an amino acid.

8. The method of claim 1, wherein the patient after administering the mixture of antibodies or antigen-binding fragments thereof, has one or more of the following characteristics:
   a) symptoms such as cough, sore throat or stuffy nose which are respiratory symptoms are mild or absent for at least 24 hours;
   b) symptoms such as headache, fever, induced pain, or fatigue which are systemic symptoms are mild or absent for at least 24 hours; or
   c) the body temperature is maintained at 37.8° C. or less for at least 24 hours.

9. The method of claim 1, wherein the patient before administering the mixture of antibodies or antigen-binding fragments thereof, has one or more of the following characteristics:
   a) the patient with two or more of respiratory symptoms such as cough, sore throat, or stuffy nose, or systemic symptoms such as headache, fever, induced pain, and fatigue;
   b) the patient with high fever of 38.0° C. (100.4° F.) or more at screening, or high fever within 24 hours before screening, but receiving antipyretic treatment within 6 hours before screening; or c) the patient who do not have a history of administration of an antiviral agent within 14 days prior to administration of the mixture.

10. A kit comprising:
(a) a composition comprising a mixture of two or more different anti-influenza virus antibodies or antigen-binding fragments thereof; and
(b) instructions directed for administering a mixture of the antibody or antigen-binding fragment thereof at a dose of 10 to 120 mg/kg to treat a patient with an influenza virus-related disease;
wherein the mixture of two or more different anti-influenza virus antibodies or antigen-binding fragments thereof comprises:
i) antibodies or antigen-binding fragments thereof comprising a light chain variable region comprising a CDR1 region of SEQ ID NO: 1, a CDR2 region of SEQ ID NO: 2, and a CDR3 region of SEQ ID NO: 3, and a heavy chain variable region comprising a CDR1 region of SEQ ID NO: 4, a CDR2 region of SEQ ID NO: 5, and a CDR3 region of SEQ ID NO: 6; and
ii) antibodies or antigen-binding fragments thereof comprising a light chain variable region comprising a CDR1 region of SEQ ID NO: 7, a CDR2 region of SEQ ID NO: 8, and a CDR3 region of SEQ ID NO: 9, and a heavy chain variable region comprising a CDR1 region of SEQ ID NO: 10, a CDR2 region of SEQ ID NO: 11, and a CDR3 region of SEQ ID NO: 12.

* * * * *